United States Patent
Favre et al.

(10) Patent No.: US 6,617,474 B2
(45) Date of Patent: Sep. 9, 2003

(54) PROCESS FOR THE HYDROFORMYLATION OF OLEFINICALLY UNSATURATED COMPOUNDS IN A NON-AQUEOUS IONIC SOLVENT

(75) Inventors: Frédéric Favre, Saint Fons (FR); Dominique Commereuc, Meudon (FR); Hélène Olivier-Bourbigou, Rueil Malmaison (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 0 days.

(21) Appl. No.: 10/053,706

(22) Filed: Jan. 24, 2002

(65) Prior Publication Data

US 2002/0099243 A1 Jul. 25, 2002

(30) Foreign Application Priority Data

Jan. 24, 2001 (FR) .............................. 01 00970

(51) Int. Cl.$^7$ ................................................ C07C 45/50
(52) U.S. Cl. ........................................ 568/451; 568/454
(58) Field of Search .................................. 568/451, 454

(56) References Cited

U.S. PATENT DOCUMENTS 3,565,823 A  *  2/1971  Parshall
3,832,391 A  *  8/1974  Parshall
5,874,638 A  *  2/1999  Chauvin et al.

FOREIGN PATENT DOCUMENTS

| DE | 19919495 A1 | 11/2000 |
|----|-------------|---------|
| EP | 0776880 A1  | 6/1997  |

* cited by examiner

*Primary Examiner*—Johann Richter
*Assistant Examiner*—Sikarl A. Witherspoon
(74) *Attorney, Agent, or Firm*—Millen, White, Zelano & Branigan, P.C.

(57) ABSTRACT

A process for the hydroformylation of an olefinically unsaturated compound in the liquid phase by reaction, in a reaction section, with carbon monoxide and hydrogen in the presence of a polar phase comprising:

a non-aqueous ionic liquid which is at least partly miscible with the reaction products and comprises a salt of general formula $Q^+A^-$, in which $Q^+$ represents a quaternary ammonium and/or phosphonium and $A^-$ represents an anion;

and a catalyst comprising a compound or a complex of a transition metal of groups 8, 9 and 10, optionally co-ordinated with a ligand containing at least one atom of phosphorus, arsenic, antimony or nitrogen, comprises addition to the medium, after the reaction section, of an organic solvent in a manner such as to improve the separation by demixing of the crude reaction products from the said polar phase, which is recycled to the reaction section.

33 Claims, 2 Drawing Sheets

PROCESS FOR THE HYDROFORMYLATION OF OLEFINICALLY UNSATURATED COMPOUNDS IN A NON-AQUEOUS IONIC SOLVENT

BACKGROUND OF THE INVENTION

1. Field of the Invention

The present invention relates to an improved process for the hydroformylation of olefinically unsaturated compounds. The invention also relates to an installation for carrying out the said process.

The hydroformylation of olefinic compounds is a reaction of great industrial importance, and the majority of processes utilize homogeneous catalysts dissolved in an organic phase made up of the reagents, the products and, where appropriate, an excess of ligand, with the result that difficulties are encountered in separating off and recovering the catalyst, in particular if this is employed in a relatively large amount, as is the case with catalysts based on cobalt, or if this is a noble metal, as is the case with catalysts based on rhodium.

2. Description of the Prior Art

One solution aimed at solving this problem has been mentioned by Bartik et al.: Organometallics (1993) 12 164–170, J. Organometal. Chem. (1994) 480 15–21 and by Beller et al.: J. Molecular Catal. A: Chemical (1999) 143 31–39. It consists of carrying out the hydroformylation in the presence of an aqueous solution comprising a cobalt complex which is rendered water-soluble due to the presence of a phosphine-sulfonate ligand, such as the sodium salt of trisulfonated triphenylphosphine or of a trisulfonated tris-(alkylphenyl)-phosphine. The Patent Application WO-A-97/00132 describes cobalt clusters substituted by trialkoxysilylmethyl groups, which renders them soluble in water. In this manner, the organic phase containing the aldehydes is easily separated from the aqueous phase containing the catalyst.

Another solution aimed at solving this problem has been described in French Patent No. 2,314,910. It consists of carrying out the hydroformylation in the presence of an aqueous solution comprising a rhodium complex which is rendered water-soluble due to the presence of a sulfonated phosphine ligand which is itself water-soluble, such as the sodium salt of trisulfonated triphenylphosphine. In this manner, the organic phase containing the aldehydes is easily separated from the aqueous phase containing the catalyst. This technique has been the subject of a considerable number of works which have been discussed in an article by W. A. Hermann published in Angewandte Chemie International in 1993, volume 32, page 1524 et seq.

In spite of a great industrial interest in these techniques for the hydroformylation of propylene, these two-phase systems suffer from the lack of solubility of olefins in water, which leads to relatively low reaction rates, rendering them impracticable for long-chain olefins.

Furthermore, the U.S. Pat. No. 3,565,823 has described a technique consisting of dispersing a transition metal compound in a quaternary ammonium or phosphonium salt of tin or germanium of the formula $(R^1R^2R^3R^4Z)YX_3$, in which $R^1$, $R^2$, $R^3$ and $R^4$ are hydrocarbon radicals having up to 18 carbon atoms, Z is nitrogen or phosphorus, Y is tin or germanium and X is a halogen, for example chlorine or bromine. The patent U.S. Pat. No. 3,832,391 has described a process for the carbonylation of olefins by the same composition. The above compositions have the disadvantage of having a relatively high melting point, for example above 90° C., which complicates handling of solutions of the catalyst and reaction products.

It has been indicated in U.S. Pat. No. 5,874,638 that it is possible to benefit from the advantages of using two phases while at the same time limiting the disadvantages associated on the one hand with the use of water and on the other hand with the use of compounds of high melting point by dissolving certain catalytic compounds of transition metals of groups 8, 9 and 10 of the periodic table, which are known to catalyse hydroformylation, in non-aqueous ionic solvents comprising organic-inorganic salts which are liquid at ambient temperature.

SUMMARY OF THE INVENTION

It has now been found that it was possible to increase the rates of reaction considerably by carrying out the reaction in an ionic liquid which is partly or completely miscible with the reaction products, while preserving the benefit of separating off and re-using the ionic liquid containing the catalyst and improving the yield of the reaction products by injecting, after the reaction section, an organic solvent (which can advantageously be the olefinically unsaturated compound to be hydroformylated) which is of low miscibility or immiscible with the ionic liquid and which improves demixing of the products from the remainder of the reaction effluent.

This process procedure allows the advantages of a homogeneous catalytic system to be combined with providing better utilization of the catalyst and a better yield of the products.

DETAILED DESCRIPTION OF THE INVENTION

In a general manner, the invention provides a process for the hydroformylation of at least one olefinically unsaturated compound in the liquid phase, in which at least one olefinically unsaturated compound is reacted, in a reaction section, with carbon monoxide and hydrogen in the presence of at least one non-aqueous ionic liquid, which is liquid at the reaction temperature and at least partly miscible with the reaction products, the ionic liquid comprising at least one salt of general formula $Q^+A^-$, in which $Q^+$ represents a quaternary ammonium and/or a quaternary phosphonium and $A^-$ represents an anion, and in the presence of at least one catalyst comprising at least one compound or one complex of a transition metal of groups 8, 9 and 10 of the periodic table, optionally co-ordinated with at least one ligand containing at least one atom of phosphorus (phosphorus-containing ligand), arsenic, antimony or nitrogen (nitrogen-containing ligand), the said process being characterized in that, after the reaction section, at least one organic solvent is added to the medium in a manner such as to improve the yield of the reaction products.

More particularly, the process of the invention can be used according to a procedure comprising at least the following three sections:

a) at least one section 1, in which the hydroformylation reaction is carried out as indicated above, b) at least one section 2, in which is carried out
mixing of the effluent from the reaction section with at least one organic solvent for the purpose of improving the yield of the products;
separation of the reaction products and the polar phase containing the ionic liquid and the catalyst;
and decanting of the polar phase containing the ionic liquid and the catalyst, which is recycled to the reactor of section 1 for re-use;

c) at least one section 3, in which the reaction products, the organic solvent, which is recycled into the mixing zone of section 2, and the unreacted olefinically unsaturated compound to be hydroformylated, which is recycled to section 1, are separated by distillation.

In section 3, depending on whether the organic solvent used has a higher or lower boiling point than that of the olefinically unsaturated compound to be hydroformylated, separation of the crude reaction products and the olefinically unsaturated compound to be hydroformylated is first carried out, and then separation of the final reaction products and the organic solvent, or separation of the crude reaction products and the organic solvent is first carried out, and then separation of the final reaction products from the olefinically unsaturated compound to be hydroformylated.

In a preferred variant of the process of the invention, the said organic solvent used to improve the separation of the reaction products comprises the unreacted olefinically unsaturated compound to be hydroformylated. It is then separated by distillation in section 3 and recycled at least in part to the mixing operation of section 2 and recycled in part to the reaction section 1. A particular advantage of this embodiment of the process of the invention is that it necessitates the use of only one distillation operation.

The olefinically unsaturated compounds which can be hydroformylated are chosen from the group formed by monoolefins, diolefins, and in particular conjugated diolefins, the olefinic compounds containing one or more heteroatoms, in particular in unsaturated groups, such as the ketone or carboxylic acid function. There may be mentioned by way of examples hydroformylation of pentenes into hexanal and methylpentanal, of hexenes into isoheptanals, of isooctenes into isononanals, or of olefinic $C_{10}$ to $C_{16}$ cuts into $C_{11}$ to $C_{17}$ aldehydes.

The organic solvent is chosen in a manner such as to improve the demixing of the products. More particularly, it is chosen from aliphatic, cyclic or acyclic, saturated or unsaturated hydrocarbons and aromatic or substituted aromatic hydrocarbons. Among these, the organic solvent may preferably be chosen from normal paraffins and isoparaffins and cyclic aliphatic hydrocarbons. More preferably, the organic solvent could comprise the olefinically unsaturated compound or compounds to be hydroformylated.

In the non-aqueous ionic solvent of general formula $Q^+A^-$, the anion $A^-$ is chosen in a manner such that the salt $Q^+A^-$ is liquid at a low temperature, that is to say below 90° C.

The preferred anions $A^-$ will thus be the following ions: nitrate, sulfate, phosphate, acetate, halogenoacetates, tetrafluoroborate, tetraalkylborates, tetraarylborates, hexafluoro-phosphate, hexafluoroantimonate, fluorosulfonate, perfluoroalkylsulfonates, arene-sulfonates, the latter being optionally substituted by halogen or halogenoalkyl groups, and also bis-perfluoroalkylsulfonylamides.

The quaternary ammonium and/or phosphonium cations $Q^+$ correspond in particular to the general formulae $NR^1R^2R^3R^{4+}$ and $PR^1R^2R^3R^{4+}$ or to the general formulae $R^1R^2N=CR^3R^{4+}$ and $R^1R^2P=CR^3R^{4+}$, where $R^1$, $R^2$, $R^3$ and $R^4$ are identical or different and represent hydrogen (with the exception of the cation $NH_4^+$ for $NR^1R^2R^3R^{4+}$), preferably a single substituent representing hydrogen, or hydrocarbon radicals having 1 to 30 carbon atoms, for example saturated or unsaturated alkyl groups, cycloalkyl groups or aromatic, aryl or aralkyl groups, which are optionally substituted.

The quaternary ammonium and/or phosphonium cations can also be derived from nitrogen- and/or phosphorus-containing heterocyclic radicals containing 1, 2 or 3 nitrogen and/or phosphorus atoms, in which the rings are made up of 4 to 10 atoms, preferably 5 to 6 atoms.

The quaternary ammonium and/or phosphonium cations can also correspond to one of the formulae:

in which $R^1$, $R^2$ and $R^3$ are identical or different and are as defined above and R represents an alkylene or phenylene radical.

Among the $R^1$, $R^2$, and $R^3$ and $R^4$ groups there may be mentioned the methyl, ethyl, propyl, isopropyl, butyl, secondary butyl, tertiary butyl, amyl, phenyl or benzyl radicals; $R^5$ could be a methylene, ethylene, propylene or phenylene group.

The quaternary ammonium and/or phosphonium cations $Q^+$ are preferably chosen form the group formed by N-butylpyridinium, N-ethylpyridinium, pyridinium, 3-ethyl-1-methylimidazolium, 3-butyl-1-methylimidazolium, 1-hexyl-3-methylimidazolium, diethyl-pyrazolium, N-butyl-N-methylpyrrolidinium, trimethylphenylammonium, tetrabutyl-phosphonium and tributyl-(tetradecyl)-phosphonium.

By way of examples of salts which can be used according to the invention there may be mentioned N-butylpyridinium hexafluorophosphate, N-ethyl-pyridinium tetrafluoroborate, pyridinium fluorosulfonate, 3-butyl-1-methylimidazolium tetrafluoroborate, 3-butyl-1-methylimidazolium hexafluoroantimonate, 3-butyl-1-methylimidazolium hexafluoro-phosphate, 3-butyl-1-methylimidazolium trifluoroacetate, 3-butyl-1-methylimidazolium trifluoromethylsulfonate, trimethyl-phenylammonium hexafluorophosphate, 1-hexyl-3-methylimidazolium trifluoroacetate and 3-butyl-1-methylimidazolium bis [(trifluoromethane) sulfonyl]amide. These salts can be used by themselves or as a mixture.

The transition metal compounds which can be used according to the invention are generally all the compounds of transition metals of groups 8, 9 and 10, and in particular those known to a person skilled in the art for the hydroformylation of olefins. They can be complexed or associated with an organic ligand. They can be used by themselves or as a mixture. They can also be used in the form of salts, which can be totally inorganic, for example, but not preferably, in the form of halides. They are, inter alia, compounds of cobalt, rhodium, iridium, ruthenium, palladium and platinum.

Association of organic ligands with all these compounds can advantageously be provided. These organic ligands can be ligands which carry an atom of phosphorus (phosphorus-containing ligands), arsenic (for example arsines) or antimony (for example stilbines). They can also be nitrogen-containing ligands.

The nitrogen-containing ligand is chosen from the group formed by monoamines, di-, tri- and polyamines, imines, diimines, pyridines, bipyridines, imidazoles, pyrroles and pyrazoles.

There may be mentioned by way of non-limiting examples triethylamine, ethylene-diamine, tetramethylethylenediamine, diethylenetriamine, diazabicyclooctane, 1,4,7-trimethyl-1,4,7-triazacyclononane, N,N'-dimethyl-ethane-1,2-diimine, N,N'-di-t-butyl-ethane-1,2-diimine, N,N'-di-t-butyl-butane-2,3-diimine, N,N'-diphenyl-ethane-1,2-diimine, N,N'-bis-(2,6-dimethylphenyl)-ethane-1,2-diimine, N,N'-bis-(2,6-diisopropylphenyl)-ethane-1,2-diimine, N,N'-bis-(2,6-di-t-butylphenyl)-ethane-1,2-diimine, N,N'-diphenyl-butane-2,3-diimine, N,N'-bis-(2,6-dimethylphenyl)-butane-2,3-diimine, N,N'-bis-(2,6-diisopropyl-phenyl)-butane-2,3-diimine, N,N'-bis-(2,6-di-t-butylphenyl)-butane-2,3-diimine, pyridine, picolines, t-butylpyridine, bipyridine, di-t-butyl-bipyridine, imidazole, N-methylimidazole, N-butylimidazole, benzimidazole, pyrrole, N-methylpyrrole and 2,6-dimethylpyrrole.

The nitrogen-containing ligand can also contain other organic functions, such as, for example, alcohol, aldehyde, ketone, acid, ester or nitrile functions. There may be mentioned by way of non-limiting examples picolinic acids and esters, 2,6-dialkoxypyridines, salicylaldimines, 2,6-bis-N-aryliminopyridines, 1-dialkyl- and 1-diaryl-phosphino-2-(4-pyridyl)-ethanes, alkyl (4-pyridiyl)-2-acetates, alkyl (2-pyridyl)-2-acetates, ethylene glycol bis-(4-pyridyl)-3-propanoate, (2-pyridyl)-2-ethanol, (2-pyridyl)-3-propanol and (2-pyridyl)-3-propyl acetate.

The phosphorus-containing ligand is chosen from the group formed by tertiary phosphines, polyphosphines, phosphine oxides, phosphites, phosphine-phosphite chelates or phosphine phosphine-oxide or phosphine-phosphite oxide. There may be mentioned by way of non-limiting examples the following ligands: triphenylphosphine, triphenyl phosphite and triphenylphosphine oxide.

These ligands can additionally carry, on the heteroatom and/or the hydrocarbon chain, at least one other function, such as amine, ammonium, alcohol, carboxylic acid, sulfonate, phosphonate, ether, phosphonium or sulfonium. There may be mentioned by way of non-limiting examples the following ligands: the ligand 1-(4-pyridiyl)-2-(dicyclopentylmethyl-phosphonium)-ethane tetrafluoroborate (1), the ligand 1-(N-imidazolyl)-2-(dicyclopentyl-methyl-phosphonium)-ethane tetrafluoroborate (2), the ligand 1-(diphenylphosphino)-2-(4-N-methyl-pyridinium)-ethane hexafluorophosphate (3), the ligand 1-(dicyclopentylphosphino)-2-(3-methyl-1-imidazolium)-ethane hexafluorophosphate (4)

1

2

3

4

R=Me, X=BF$_4$, Y=PF$_6$ the ligand N-(3-diphenylphosphinophenyl)-N'-dimethyl-guanidinium tetrafluoroborate (5), the ligand tris-(tetrabutylammonium phenyl-3-sulfonate)-phosphine (tetrabutylammonium triphenylphosphine-trisulfonate) (6), the ligand tris-(sodium phenyl-3-sulfonate)-phosphine (or sodium triphenylphosphine-trisulfonate or TPPTS) (7), the ligand sodium triphenylphosphine-monosulfonate (or TTPMS) and the ligand (di-t-butyl-3,5-catecholato)-(tetrabutylammonium phenoxy-4-sulfonate)-phosphite (8)

5

6

7

The catalytic composition is obtained by mixing, in any manner, the liquid salt with the transition metal compound and, where appropriate, the ligand.

The components used in the composition according to the invention can be mixed in any order at a temperature of between −20° C. and 200° C., and preferably between 0° C. and 140°, and advantageously between 20° C. and 90° C.

The complex can be prepared in situ by mixing the precursor of the transition metal and the ligand directly in the hydroformylation reactor.

The concentration of the transition metal compound in the liquid ionic solvent is not critical. It is advantageously between 0.1 mmol per liter of liquid ionic solvent and 5 mol per liter, preferably between 1 mmol and 1 mol per liters, and even between 10 and 500 mmol per liter. The molar ratio between the ligand and the transition metal compound is between 0.1 and 500, preferably between 1 and 100.

The ratio of the partial pressures of hydrogen to carbon monoxide used in the reaction medium for the hydroformylation can be from 10:1 to 1:10, preferably in a ratio of 1:1, but any other ratio can be used, depending on the process procedure.

The temperature at which the hydroformylation will take place will be between 30° C. and 200° C.; it is advantageously below 150° C., preferably between 50° C and less than 150° C. The pressure can be between 1 MPa and 20 MPa, preferably between 2 MPa and 15 MPa.

The temperature and/or the pressure during the addition of the solvent are advantageously chosen such that they are less than or equal to those used in the reaction section.

The invention also relates to an installation for carrying out the improved hydroformylation process as defined in the above description, the said installation comprising:
   at least one reactor A1;
   at least one mixer A2 for mixing the effluent from the reactor A1 with at least one organic solvent;
   and at least one decanter B2 for decanting the polar phase containing at least the ionic liquid containing at least the catalyst, which is recycled to the reactor A1;
and also
   at least one pipe 1 for introduction of the batch to be hydroformylated and of the carbon monoxide/hydrogen mixture;
   at least one pipe 5 for introduction of the effluent from the reactor into the mixer A2;
   at least one pipe 9 for introduction of the organic solvent into the mixer A2;
   at least one pipe 6 for sending the mixture of the effluent and the organic solvent contained in the mixer A2 to the decanter B2; and
   at least one pipe 7 which allows the polar phase containing at least the ionic liquid and the catalyst separated in B2 back into the reactor A1; and
   at least one pipe 8 which allows the crude reaction products to be withdrawn from the decanter B2.

If the organic solvent used has a boiling point above that of the olefinically unsaturated compound to be hydroformylated, the installation according to the invention also comprises:
   in the separation section 3, at least one column A3 for separation of the crude reaction products and the unreacted olefinically unsaturated compound to be hydroformylated and at least one column B3 which allows separation of the organic solvent from the final reaction products;
and also
   at least one pipe 4 for recycling the unreacted olefinically unsaturated compound to be hydroformylated separated off in the column A3 to the reactor A1;
   at least one pipe 10 which allows the products leaving the bottom of the column A3 to be sent into the column B3; and
   at least one pipe 11 which allows the final reaction products to be collected.

If the organic solvent used has a boiling point below that of the olefinically unsaturated compound to be hydroformylated, the installation of the invention also comprises:
   in the separation section 3, at least one column B3 which allows separation of the organic solvent from the crude reaction products and at least one column A3 for separation of the final reaction products and the unreacted olefinically unsaturated compound to be hydroformylated;
and also
   at least one pipe 4 for recycling the unreacted olefinically unsaturated compound to be hydroformylated separated off in the column A3 to the reactor A1;
   at least one pipe 10 which allows the products leaving the bottom of the column B3 to be sent into the column A3; and
   at least one pipe 11 which allows the final reaction products to be collected.

If the organic solvent used comprises the olefinically unsaturated compound to be hydroformylated itself, the installation of the invention also comprises:
   in the separation section 3, a column A3 which allows separation of the unreacted olefinically unsaturated compound to be hydroformylated and the final reaction products;
and also
   leaving this column A3, a pipe for evacuation of the unreacted olefinically unsaturated compound to be hydroformylated, the said pipe dividing into two pipes, the pipe 9 for sending at least a fraction of the said olefinically unsaturated compound into the mixer A2 as the organic solvent, and a pipe 4 for recycling a fraction of the said olefinically unsaturated compound to the intake of the reactor A1; and
   at least one pipe 11 which allows the final reaction products to be collected.

Figure 1:
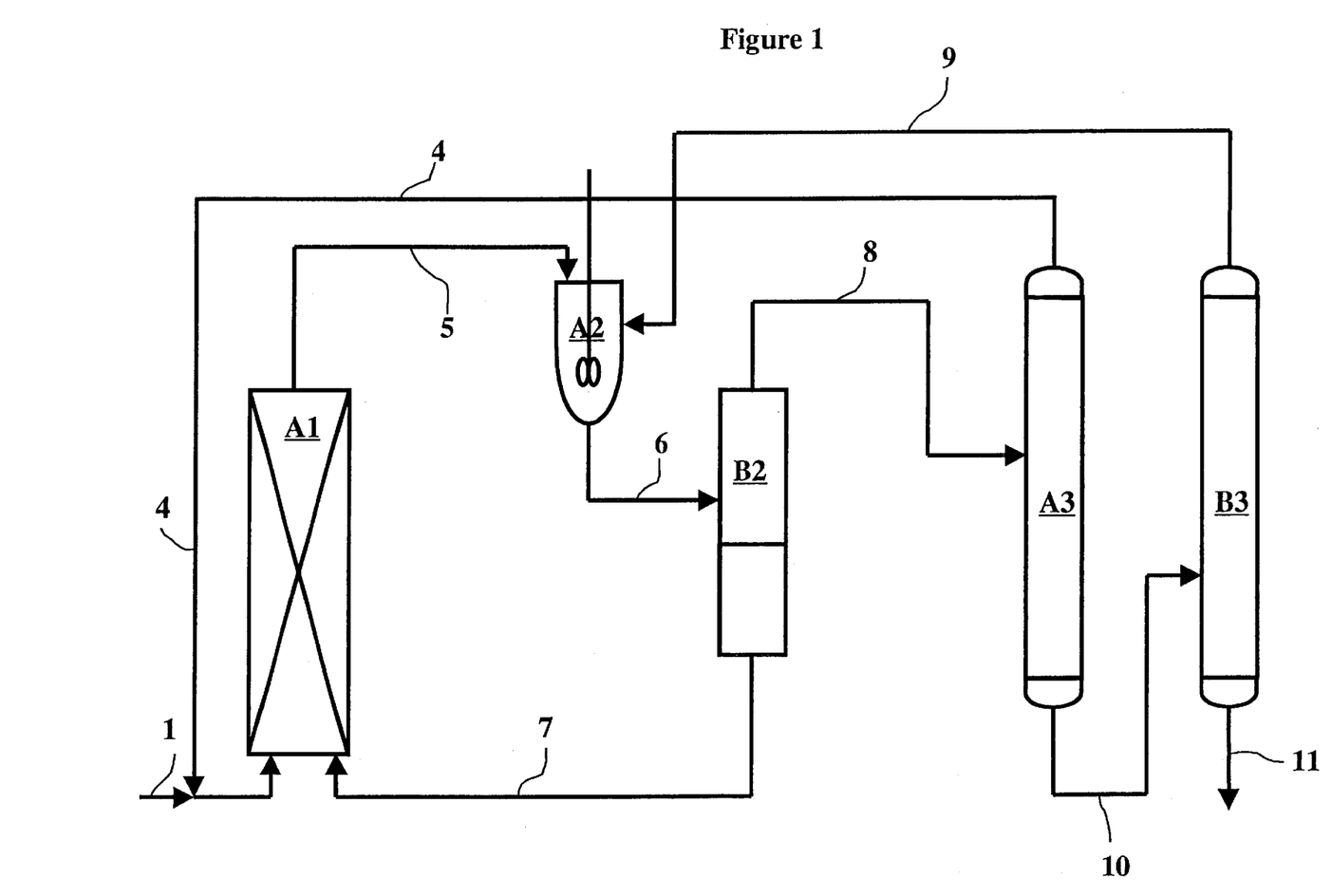
FIG. 1 illustrates an embodiment of an installation of the invention comprising 3 sections, in which the organic solvent chosen has a boiling point higher than the compound to be hydroformylated.
Figure 2:
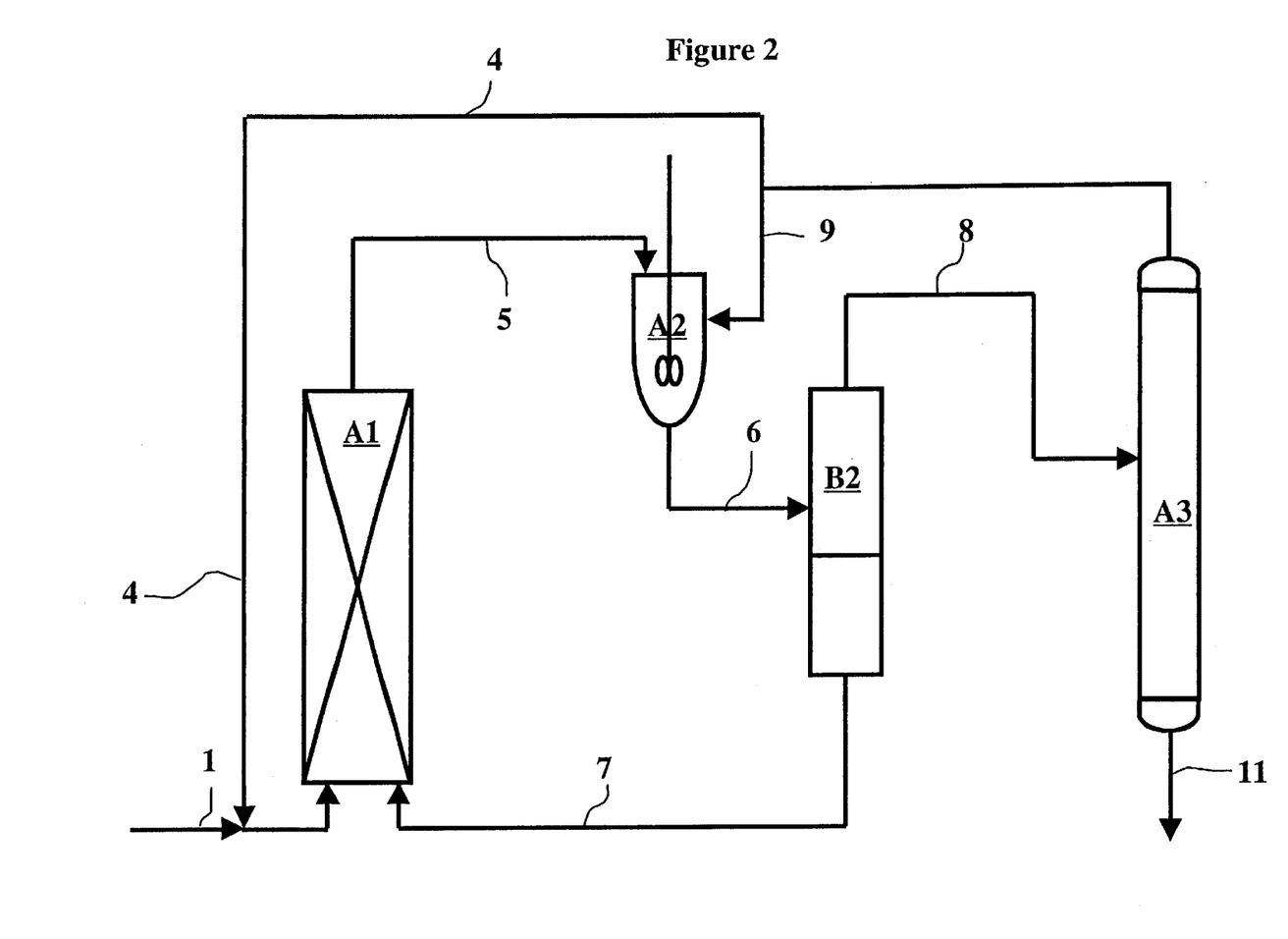
FIG. 2 illustrates the preferred variant of the process of the invention, according to which the organic solvents comprises the olefinically unsaturated compound to be hydroformylated.

The process and installation of the invention will be understood better from the description which follows, together with FIGS. 1 and 2.

FIG. 1 illustrates an embodiment of an installation with 3 sections, in which the organic solvent chosen has a boiling point higher than the compound to be hydroformylated. According to another option, the organic solvent can also have a boiling point below that of the reagents and products.

According to FIG. 1, the reaction is carried out in the reactor A1 in the presence of the batch to be hydroformylated, which can be introduced via line 1, the transition metal compound(s), the organic ligand (which can optionally be introduced as a mixture with the transition metal compound or compounds), carbon monoxide and hydrogen, which can be introduced via line 1, and in the presence of at least one ionic liquid, used in the liquid phase, in a homogeneous or two-phase medium. The ionic liquid can be introduced into the reactor at the start of the reaction. Optionally, fresh ionic liquid can be injected into the reactor A1 during the reaction and spent ionic liquid can be withdrawn from A1.

The heat of reaction is removed by techniques known to a person skilled in the art, which are not shown on FIG. 1.

At the exit of the reaction section, the effluent from the reactor is sent via line 5 into at least one mixer A2, into which is injected, via line 9, an organic solvent which improves demixing of the reaction products. The effluent is then withdrawn from the mixer A2 and sent into a decanter B2 via line 6. In this decanter B2 the polar phase, which contains at least the ionic liquid and the catalyst, is separated from the mixture of the products and the organic solvent and is sent back to the reactor A1 via line 7. The polar phase sent back in this manner can optionally contain a fraction of the organic solvent.

The reaction products, mixed with the organic solvent, are sent into a first distillation column A3 via line 8. In the column A3 the unreacted olefinically unsaturated compound to be hydroformylated is separated off at the top; it is recycled to the reactor A1 via line 4. The products and the solvent are sent into a column B3 via line 10. In this column B3, and in one embodiment, the organic solvent is separated off at the top of the column, in the option where it is lighter than the products, and sent into the mixer A2 via line 9. At the bottom of the column B3 the products are collected via line 11. They can then be sent into a subsequent fractionation zone if necessary.

The column A3 is installed upstream of the column B3 or vice versa, depending on whether the boiling point of the organic solvent is higher or lower than that of the compound to be hydroformylated.

FIG. 2 illustrates the preferred variant of the process of the invention, according to which the organic solvents comprises the olefinically unsaturated compound to be hydroformylated. This option has the advantage of using one distillation column less in section 3.

According to FIG. 2, the reaction is carried out in the reactor A1 in the presence of the batch to be hydroformylated, which can be introduced via line 1, the transition metal compound(s), the organic ligand (which can be introduced as a mixture with the transition metal compound or compounds), carbon monoxide and hydrogen, which can be introduced via line 1, and in the presence of at least one ionic liquid, used in the liquid phase, in a homogeneous or two-phase medium. The ionic liquid can be introduced into the reactor at the start of the reaction. Fresh ionic liquid can be injected, if appropriate, into the reactor A1 during the reaction and spent ionic liquid can be withdrawn from the reactor A1.

The heat of reaction is removed by techniques known to a person skilled in the art, which are not shown on FIG. 2.

At the exit of the reaction section, the effluent from the reactor is sent via line 5 into at least one mixer A2, into which is injected, via line 9, an organic solvent which improves demixing of the reaction products. In the option described by FIG. 2, this organic solvent advantageously comprises the reagent or reagents.

The effluent is then withdrawn from the mixer A2 and sent into a decanter B2 via line 6. In this decanter B2 the polar phase, which contains at least the ionic liquid and the catalyst, is separated from the mixture of the products and the organic solvent and is sent back to the reactor A1 via line 7.

The reaction products and the solvent are sent via line 8 into the distillation column A3. In one embodiment option, the reagents are separated off at the top of the column and sent via line 9 into the mixer A2. At the bottom of the column A3 the products are collected via line 11. They can then be sent into a subsequent fractionation zone if necessary.

In the option illustrated by FIG. 2, the flow rate of the recycling of the compound to be hydroformylated (line 9) is adjusted such that the major portion of the products demix in the decanter B2.

The following examples illustrate the invention without limiting its scope.

EXAMPLE 1

The hydroformylation reaction of 1-hexene is carried out in a stainless steel autoclave with a capacity of 100 ml fitted with a double jacket which allows regulation of the temperature by circulation of a heat transfer liquid. Into this autoclave, which has been purged of air and moisture beforehand and placed under an atmospheric pressure of a hydrogen/carbon monoxide mixture (1/1 molar), 0.0193 g rhodiumdicarbonyl acetylacetonate (that is to say 0.075 mmol rhodium), 4 molar equivalents of sodium triphenylphosphine-trisulfonate, 4 ml of the ionic liquid 3-butyl-1-methylimidazolium trifluoroacetate and 7.5 ml 1-hexene are introduced. The pressure of the hydrogen/carbon monoxide mixture (1/1 molar) is brought to 2 MPa and the temperature is brought to 80° C., and stirring is started. After 1 hour, the stirring is stopped and the reaction mixture is allowed to cool and the pressure is then released. The effluent from the reactor is withdrawn. The majority of the organic phase is miscible in the ionic liquid. 8 ml heptane are added, which causes demixing of the products.

The organic phase is analysed by gas chromatography. The conversion of hexene is 97%. The selectivity for aldehydes is 98% and the n/i (n-heptanal/isoheptanals) ratio is 3.1. The rotation frequency is calculated at 25% conversion. It is equal to 33 mol of aldehydes formed per mol of rhodium and per hour.

EXAMPLE 2

The hydroformylation reaction of 1-hexene is carried out in the same apparatus and in accordance with the same method of operation as described in Example 1, except that the nature of the cation constituting the ionic liquid is changed. Into this autoclave, which has been purged of air and moisture beforehand and placed under an atmospheric pressure of a hydrogen/carbon monoxide mixture (1/1 molar), 0.0193 g rhodiumdicarbonyl acetylacetonate (that is to say 0.075 mmol rhodium), 4 molar equivalents of sodium triphenylphosphine-trisulfonate, 4 ml of the ionic liquid 1-hexyl-3-methylimidazolium trifluoroacetate and 7.5 ml 1-hexene are introduced. The pressure of the hydrogen/carbon monoxide mixture (1/1 molar) is brought to 2 MPa and the temperature is brought to 80° C., and stirring is started. After 1 hour, the stirring is stopped and the reaction mixture is allowed to cool and the pressure is then released. The effluent from the reactor is withdrawn. The effluent from the reactor is made up of a single liquid phase. 8 ml heptane are added, which causes demixing of the products.

The organic phase is analysed by gas chromatography. The conversion of-hexene is total. The selectivity for aldehydes is 99% and the n/i ratio (n-heptanal/isoheptanals) is 2.9. The rotation frequency is calculated at 25% conversion. It is equal to 60 mol of aldehydes formed per mol of rhodium and per hour. The initial rate of the reaction is thus considerably improved by using an ionic liquid which has a higher affinity for aldehydes.

EXAMPLE 3
(recovery of rhodium in the ionic liquid)

The hydroformylation reaction of 1-hexene is carried out as in Example 1 and 2. Into the autoclave, which has been purged of air and moisture beforehand and placed under an atmospheric pressure of a hydrogen/carbon monoxide mixture (1/1 molar), 0.0193 g rhodiumdicarbonyl acetylacetonate (that is to say 0.075 mmol rhodium), 4 molar equivalents of sodium triphenylphosphine-trisulfonate, 4 ml 3-butyl-1-methylimidazolium bis [(trifluoro-methane) sulfonyl]-amide and 7.5 ml 1-hexene are introduced. The pressure of the hydrogen/carbon monoxide mixture (1/1 molar) is brought to 2 MPa and the temperature is brought to 80° C., and stirring is started. After 1 hour, the stirring is stopped and the reaction mixture is allowed to cool and the pressure is then released. After withdrawal from the autoclave, the reaction mixture is composed of a single liquid phase. 8 ml heptane are added, which causes demixing of the products into a 2nd phase. The conversion of 1-hexene is 99% by weight. The selectivity for C7 aldehydes is 93% and the n/iso (n-heptanal/isoheptanals) ratio is equal to 3.5. Analysis of the upper organic phase shows that it contains less than 5 ppm of rhodium metal (ppm: parts per million by weight), which corresponds to less than 0.2% by weight of the metal employed.

The upper organic phase obtained, which contains heptane and the reaction products, is distilled to separate off the heptane.

The lower ionic phase is re-injected into the autoclave, which has been purged of air and moisture beforehand and placed under an atmospheric pressure of the hydrogen/carbon monoxide mixture (1/1 molar). 7.5 ml 1-hexene are then introduced. The pressure of the hydrogen/carbon monoxide mixture (1/1 molar) is brought to 2 MPa and the temperature is brought to 80° C., and stirring is started. After 1 hour, the stirring is stopped and the reaction mixture is allowed to cool and the pressure is then released. After withdrawal from the autoclave the reaction mixture is composed of a single liquid phase. The heptane recovered by distillation of the first batch of Example 3 is then added, which causes demixing of the products into a 2nd phase. The conversion of 1-hexene is 98% by weight. The selectivity for C7-aldehydes is 93% and the n/iso (n-heptanals/isoheptanals) ratio-is equal to 3.5.

EXAMPLE 4

The hydroformylation reaction is carried out as in Example 3. Into the autoclave, which has been purged of air and moisture beforehand and placed under an atmospheric pressure of a hydrogen/carbon monoxide mixture (1/1 molar), 0.0193 g rhodiumdicarbonyl acetylacetonate (that is to say 0.075 mmol rhodium), 4 molar equivalents of sodium triphenylphosphine-trisulfonate, 4 ml 3-butyl-1-methylimidazolium bis[(trifluoromethane) sulfonyl]-amide and 7.5 ml 1-hexene are introduced. The pressure of the hydrogen/carbon monoxide mixture (1/1 molar) is brought to 2 MPa and the temperature is brought to 80° C., and stirring is started. After 1 hour, the stirring is stopped and the reaction mixture is allowed to cool and the pressure is then released. After withdrawal from the autoclave, the reaction mixture is composed of a single liquid phase. 8 ml 1-hexene are added, which causes, in the same manner as with heptane described in Example 3, demixing of the products into a 2nd phase. The conversion of 1-hexene, calculated with respect to 7.5 ml 1-hexene introduced at the start of the reaction, is 99% by weight. The selectivity for C7 aldehydes is 93% and the n/iso (n-heptanal/isoheptanals) ratio is equal to 3.5. Analysis of the upper organic phase shows that it contains less than 5 ppm of rhodium metal (ppm: parts per million by weight), which corresponds to less than 0.2% by weight of the metal employed.

The preceding examples can be repeated with similar success by substituting the generically or specifically described reactants and/or operating conditions of this invention for those used in the preceding examples. Also, the preceding specific embodiments are to be construed as merely illustrative, and not limitative of the remainder of the disclosure in any way whatsoever.

The entire disclosure of all applications, patents and publications cited above and below, and of corresponding French application 01/00970, filed Jan. 24, 2001, are hereby incorporated by reference.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A process comprising reacting under hydroformylation conditions at least one olefinically unsaturated compound in the liquid phase in a reaction section, with carbon monoxide and hydrogen in the presence of at least one polar phase comprising:

a non-aqueous ionic liquid which is liquid at the reaction temperature and at least partly miscible with the reaction products, the ionic liquid comprising at least one salt of general formula $Q^+A^-$, in which $Q^+$ represents a quaternary ammonium and/or a quaternary phosphonium and $A^-$ represents an anion;

and at least one catalyst comprising at least one compound or one complex of a transition metal of groups 8, 9 and 10 of the periodic table, optionally co-ordinated with at least one ligand containing at least one atom of phosphorus, arsenic, antimony or nitrogen, said process further comprising withdrawing from the reaction section the resultant reaction medium, adding to the resultant reaction medium at least one organic solvent which serves to improve separation by demixing of the crude reaction products from the polar phase, and recycling separated polar phase to the reaction section for re-use.

2. A process according to claim 1, comprising at least the following three sections:

a) at least one section 1, in which the hydroformylation reaction is carried out, b) at least one section 2, in which is carried out
    mixing of the effluent from the reaction section with at least one organic solvent;
    separation of the reaction products from the polar phase containing the ionic liquid and the catalyst;
    and decanting of the polar phase containing the ionic liquid and the catalyst;

c) at least one section 3, in which the reaction products, the organic solvent, which is recycled into the mixing zone of section 2, and the unreacted olefinically unsaturated compound to be hydroformylated, which is recycled to section 1, are separated by distillation.

3. A process according to claim 2, wherein the organic solvent has a boiling point higher than that of the olefinically unsaturated compound to be hydroformylated, the separation of the crude reaction products and the olefinically unsaturated compound to be hydroformylated is first carried out, and then the separation of the final reaction products and the organic solvent.

4. A process according to claim 2, wherein the organic solvent has a boiling point lower that that of the olefinically unsaturated compound to be hydroformylated, the separation of the crude reaction products and the organic solvent is first carried out, and then the separation of the final reaction products from the olefinically unsaturated compound to be hydroformylated.

5. A process according to claim 1, wherein said olefinically unsaturated compound to be hydroformylated is chosen from the group consisting of monoolefins, diolefins, conjugated diolefins and olefinic compounds containing one or more heteroatoms.

6. A process according to claim 1, wherein the organic solvent is selected from the group consisting of aliphatic cyclic or acyclic saturated or unsaturated, aromatic or substituted aromatic hydrocarbons.

7. A process according to claim 1, wherein the organic solvent is the olefinically unsaturated compound to be hydroformylated.

8. A process according to claim 1, wherein in the salt of general formula $Q^+A^-$, the anion $A^-$ is chosen such that the salt $Q^+A^-$ is liquid below 90° C.

9. A process according to claim 1, wherein the anion $A^-$ is chosen from the group consisting of nitrate, sulfate, phosphate, acetate, halogenoacetates, tetrafluoroborate, tetraalkylborates, tetraarylborates, tetrachloroborate hexafluorophosphate, hexafluoroantimonate fluorosulfonate, perfluoroalkylsulfonates, arene-sulfonates, arene-sulfonates substituted by halogen or halogenoalkyl groups and bis-perfluoroalkylsulfonylamides.

10. A process according to claim 1, wherein the quaternary ammonium and/or phosphonium cation corresponds to one of general formulae:

$NR^1R^2R^3R^{4+}$ and $PR^1R^2R^3R^{4+}$ or to one of general formulae:

$R^1R^2N=CR^3R^{4x}$ and $R^1R^2P=CR^3R^{4+}$, in which $R^1$, $R^2$, $R^3$ and $R^4$ are identical or different and each represent hydrogen, with the exception of the cation $NH_4^+$ for $NR^1R^2R^3R^{4+}$.

11. A process according to claim 1, wherein the quaternary ammonium and/or phosphonium cation is derived from a nitrogen- and/or phosphorus-containing heterocyclic radical containing 1, 2 or 3 nitrogen and/or phosphorus atoms, in which the rings are made up of 4 to 10 atoms.

12. A process according to claim 1, wherein the quaternary ammonium and/or phosphonium cation corresponds to one of the formulae:

$R^1R^{2+}N=CR^3-R^5-R^3C=N^+R^1R^2$ and $R^1R^{2+}P=CR^3-R^5-R^3C=P^+R^1R^2$ in which $R^1$, $R^2$ and $R^3$ are identical or different and each represents hydrogen or a hydrocarbon radical having 1–30 carbon atoms, and $R^5$ represents an alkylene or phenylene radical.

13. A process according to claim 1, wherein the quaternary ammonium and/or phosphonium cation $Q^+$ is chosen from the group consisting of N-butylpyridinium, N-ethylpyridinium, pyridinium, 3-ethyl-1-methylimidazolium, 3-butyl-1-methylimidazolium, 1-hexyl-3-methylimidazolium, diethylpyrazolium, N-butyl-N-methylpyrrolidinium, trimethylphenylammonium, tetrabutylphosphonium and tributyl-(tetradecyl)-phosphonium.

14. A process according to claim 1, wherein the non-aqueous ionic solvent comprises at least one salt chosen from the group consisting of N-butyl-pyridinium hexafluorophosphate, N-ethyl-pyridinium tetrafluoroborate, pyridinium fluorosulfonate, 3-butyl-1-methylimidazolium tetrafluoroborate, 3-butyl-1-methyl-imidazolium hexafluoroantimonate, 3-butyl-1-methylimidazolium hexafluorophosphate, 3-butyl-1-methylimidazolium trifluoroacetate, 3-butyl-1-methyl-imidazolium trifluoromethylsulfonate, trimethyl-phenylammonium hexafluorophosphate, 1-hexyl-3-methylimidazolium trifluoroacetate and 3-butyl-1-methyl-imidazolium bis [(trifluoromethane)sulfonyl]amide.

15. A process according to claim 1, wherein the transition metal is cobalt, rhodium, iridium, ruthenium, palladium or platinum.

16. A process according to claim 1, wherein the transition metal compound is a transition metal complex.

17. A process according to claim 1, wherein the catalytic composition also comprises a ligand or a ligand associated with the transition metal compound, said ligand carrying at least one atom of phosphorus, arsenic, antimony or nitrogen.

18. A process according to claim 17, wherein the ligand is chosen from tertiary phosphines, poly-phosphines, oxides of phosphines, phosphites, phosphine-phosphite chelates, phosphine phosphine-oxide and the oxide of phosphine-phosphites, arsines, stilbines and nitrogen-containing ligands.

19. A process according to claim 18, wherein the phosphorus-containing ligand contains at least one amine, ammonium, alcohol, carboxylic acid, sulfonate, phosphonate, ether, phosphonium or sulfonium function.

20. A process according to claim 17, wherein the nitrogen-containing ligand is chosen from the group formed by monoamines, di-, tri- and polyamines, imines, diimines, pyridines, bipyridines, imidazoles, pyrroles and pyrazoles.

21. A process according to claim 1, wherein the concentration of the transition metal in the liquid ionic solvent is between 0.1 mmol per liter and 5 mol per liter and the molar ratio between the ligand and the transition metal compound is between 0.1 and 500.

22. A process according to claim 1, wherein the hydroformylation reaction is carried out with a ratio of partial pressures of hydrogen to carbon monoxide of 10:1 to 1:10, at a temperature between 30° C. and 200° C. and under a total pressure of between 1 MPa and 20 MPa.

23. A process according to claim 1, wherein the temperature and/or the pressure during the addition of the solvent are chosen such that they are less than or equal to those used in the reaction section.

24. A process according to claim 2, wherein the organic solvent is the olefinically unsaturated compound to be hydroformylated.

25. A process according to claim 3, wherein the organic solvent is the olefinically unsaturated compound to be hydroformylated.

26. A process according to claim 4, wherein the organic solvent is the olefinically unsaturated compound to be hydroformylated.

27. A process according to claim 5, wherein the organic solvent is the olefinically unsaturated compound to be hydroformylated.

28. A process according to claim 6, wherein the organic solvent is the olefinically unsaturated compound to be hydroformylated.

29. A process according to claim 2, wherein the organic solvent is chosen from the aliphatic cyclic or acyclic saturated or unsaturated, aromatic or substituted aromatic hydrocarbons.

30. A process according to claim 3, wherein the organic solvent is chosen from the aliphatic cyclic or acyclic saturated or unsaturated, aromatic or substituted aromatic hydrocarbons.

31. A process according to claim 4, wherein the organic solvent is chosen from the aliphatic cyclic or acyclic saturated or unsaturated, aromatic or substituted aromatic hydrocarbons.

32. A process according to claim 5, wherein the organic solvent is chosen from the aliphatic cyclic or acyclic saturated or unsaturated, aromatic or substituted aromatic hydrocarbons.

33. A process according to claim 1, comprising at least the following three sections:

a) at least one section 1, in which the hydroformylation reaction is carried out,
b) at least one section 2, in which is carried out
   mixing of the effluent from the reaction section with at least one organic solvent;
   separation of a phase comprising the reaction products, organic solvent and unreacted olefinically unsaturated compound from the polar phase containing the ionic liquid and the catalyst;
   and decanting of the polar phase containing the ionic liquid and the catalyst;
c) at least one section 3 comprising distillation to separate the reaction products, as a bottoms stream, from an overhead stream comprising unreacted olefinically unsaturated compound and organic solvent, and recycling part of said overhead stream to said at least one section 1 and recycling another part of said overhead stream to said at least one section 2.

* * * * *

UNITED STATES PATENT AND TRADEMARK OFFICE
CERTIFICATE OF CORRECTION

PATENT NO.     : 6,617,474 B2
DATED          : September 9, 2003
INVENTOR(S)    : Frederic Favre et al.

It is certified that error appears in the above-identified patent and that said Letters Patent is hereby corrected as shown below:

<u>Title page,</u>
Item [*] Notice, "0 days" should read -- 28 days --

Signed and Sealed this

Fourteenth Day of September, 2004

JON W. DUDAS
*Director of the United States Patent and Trademark Office*